United States Patent [19]
Revillet et al.

[11] 4,431,606
[45] Feb. 14, 1984

[54] MULTICUVETTE ROTOR FOR ANALYZER

[75] Inventors: Georges Revillet, Onex; Michel Thévoz, Neuchatel, both of Switzerland

[73] Assignee: Hoffmann-La Roche Inc., Nutley, N.J.

[21] Appl. No.: 259,346

[22] Filed: May 1, 1981

[30] Foreign Application Priority Data

May 5, 1980 [CH] Switzerland ............... 3485/80
Mar. 13, 1981 [CH] Switzerland ............... 1735/81

[51] Int. Cl.³ .................. G01N 21/07; G01N 9/30
[52] U.S. Cl. ........................ 422/102; 356/246;
422/72; 494/16
[58] Field of Search ............ 422/72, 64; 233/26;
23/230 R; 356/246; 436/45

[56] References Cited

U.S. PATENT DOCUMENTS

| | | |
|---|---|---|
| 3,744,975 | 7/1973 | Mailen .................. 436/45 |
| 3,795,451 | 3/1974 | Mailen ................. 422/72 X |
| 3,873,217 | 3/1975 | Anderson et al. ........... 422/99 |
| 3,899,296 | 8/1975 | Mailen et al. .............. 422/72 |
| 3,901,658 | 8/1975 | Burtis et al. ............. 356/246 |
| 4,244,694 | 1/1981 | Farina et al. ........... 422/72 X |
| 4,252,538 | 2/1981 | Barr .................... 422/72 X |
| 4,284,602 | 8/1981 | Kelton et al. ............. 422/72 |

FOREIGN PATENT DOCUMENTS 1432428 4/1976 United Kingdom ........... 422/72

*Primary Examiner*—Michael S. Marcus
*Attorney, Agent, or Firm*—Jon S. Saxe; Bernard S. Leon; George W. Johnston

[57] ABSTRACT

The invention relates to an analytical rotor comprising a set of analytical cells disposed at its periphery, a central distribution chamber, portioning cavities corresponding to the respective cells and disposed between the cells and the chamber periphery, the cavities each having an inlet connected to the chamber and an outlet connected to one of the cells by a transfer passage, and at least one overflow reservoir connected to the inlets of the cavities by at least one communication passage.

15 Claims, 10 Drawing Figures

MULTICUVETTE ROTOR FOR ANALYZER

BACKGROUND OF THE INVENTION

In clinical chemistry, analysis are conducted on very small samples, so that the accuracy of the results depends closely on the accuracy of the amounts of sample and reagent portions delivered to the area where the analysis is being conducted. This accuracy of amounts depends on the pipettes used to deliver the portions and is correspondingly difficult to guarantee when very small portions of materials are utilized. This has resulted in the development of high-accuracy pipettes but these high-accuracy pipettes are very expensive. In addition, the pipetting operation has to be repeated for each analyzed sample and each portion of reagent, with the result that the process of preparing a set of samples and reagents for analysis in a rotor of a centrifugal analyzer usually takes longer than the analysis itself.

Another essential factor in the accuracy of analysis is the determination of the time at which the reaction begins, i.e. when the sample is placed in the presence of the reagent. This is the reason why the cells are disposed at the periphery of the analytical rotor, which has chambers for introducing reagent and/or a sample and communicating with the respective cells, the contents of the chambers being simultaneously distributed to the cells by the centrifugal force applied to the liquids upon centrifugation of the rotor.

In U.S. Pat. No. 3,873,217 it has already been proposed to measure out and distribute the portions of the required liquid simultaneously to analytical cells disposed at the rotor periphery. The measuring-out is performed as follows: A liquid injected into a central chamber is divided among various analytical units by equidistant edges or ridges at the chamber periphery. As a result of the rotation of the rotor and the division of the liquid by the equidistant edges, the liquid is forcibly introduced into the units. The aforementioned proportioning lacks accuracy and is dependent inter alia on the amount of liquid introduced into the central chamber, so that the exact quantity has to be pipetted.

According to U.S. Pat. No. 3,744,975, portioning similar to that described in the preceding patent specification is carried out by using an overflow reservoir. The portions are simultaneously distributed to the cells by sending a stream of air under pressure. This does not ensure that a very accurage volume of liquid is transferred.

The aim of the invention is to obviate the disadvantages of the aforementioned methods by providing a high-accuracy portioning of samples and/or reagents followed by simultaneous distribution of the portions, using a device having a simple structure and adapted to be mass-produced at a reasonable price.

The analytical rotor according to the invention is characterized in that liquid-retaining means are associated with the transfer passages to prevent liquid flowing into the analytical cells until the centrifugal force applied to the liquid exceeds a threshold value which is made higher than the hydraulic resistance to flow through the communication passage.

The invention also relates to use of the analytical rotor, characterized in that a volume of liquid greater than the total volume of the portioning cavities is introduced into the distribution chamber, the rotor is driven at a first speed to exert on the liquid a centrifugal force greater than the aforementioned hydraulic resistance to flow through the communication passage but smaller than the threshold value, in order to fill the portioning cavities and discharge the surplus liquid into the overflow reservoir, and the rotor speed is changed to a secod speed greater than the first, in order to exert on the liquid a centrifugal force greater than the threshold value, so as to transfer the portions contained in the portioning cavities to the respective analytical cells.

The accompanying drawings are diagrammatic illustrations, by way of example, of various embodiments and variants or the analytical rotor according to the invention. In the drawings.

Figure 2:
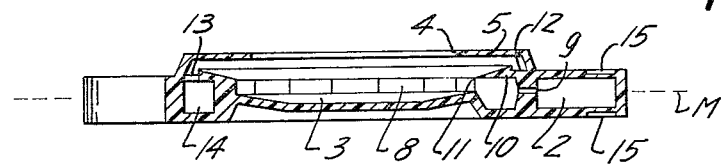
FIG. 2 is a view in section along line II—II of FIG. 1.
Figure 1:
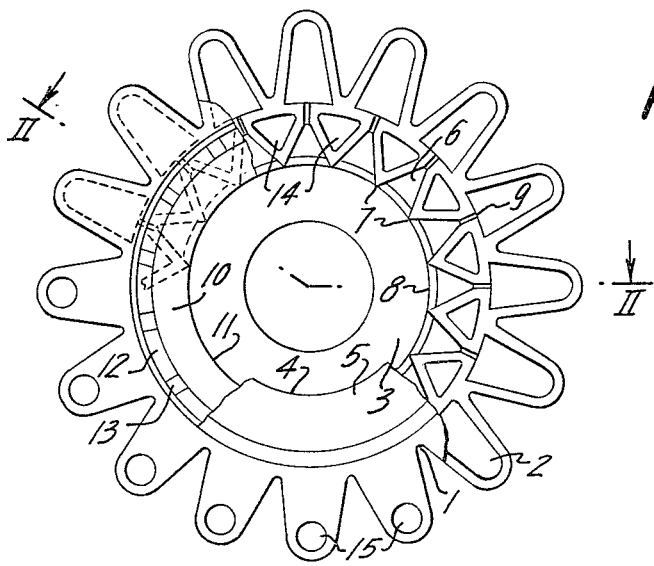
FIG. 1 is a partly cut-away plan view of a first embodiment.

FIGS. 1 and 2 show an analytical rotor in the form of a disc 1 having a set of regularly distributed analytical cells 2 at its periphery. The central region of the analytical rotor is used as a distribution chamber 3, axially communicating with the exterior via a central aperture 4 formed in the top surface 5 of the rotor. The bottom of the distribution chamber 3 is in the form of a dish having a flat central region and an annular frusto-conical edge. The periphery of the distribution chamber 3 communicates with a set of triangular portioning cavities 6. All the cavities are separated from one another by ridges or edges 7 formed by the intersection of two adjacent sides of each cavity. All the ridges 7 are arranged circumferentially about the distribution chamber. The respective bases of the triangles, adjacent the circle, open towards the distribution chamber 3. The apex of each triangle opposite its open base has an outlet aperture at the end of a transfer passage 9 connecting each portioning cavity 6 to an analytical cell 2. As shown in FIG. 2, the edge formed by the apex of the triangular cavity 6 adjacent passage 9 forms an angle smaller than 180° and the end of the transfer passage 9 and the apex lie along the same radius. This configuration facilitates emptying cavities 6 under the action of centrifugal force. The transfer passages 9 comprise capillary ducts, the cross-section of which is chosen so that the resulting capillary forces maintain a cohesive meniscus of liquid at the outlet of the transfer passage 9. To this end, each passage 9 opens into a surface of cells 2 parallel to the axis of rotation of rotor 1 and half-way from the top and bottom surface of the cells, in order to substantially reduce the risk of destabilization of the resulting meniscus.

The inlets of the portioning cavities 6 are adjacent an annular wall 10 which covers them and whose top surface is configured as an inclined plane, starting from an edge 11 of wall 10 adjacent to the inlets 8. The inclined plane terminates in an annular collector 12, the bottom of which has apertures 13 giving access to triangular overflow reservoirs 14 each inserted between two adjacent portioning cavities 6. The cross-sections of the respective apertures 13 are made sufficiently large to prevent capillary force being exerted on the liquid flowing through them.

Each cell 2 comprises two windows 15 disposed opposite one another along an axis parallel to the axis of rotation of rotor 1. The windows are for photometrically measuring the contents of the cells.

Rotors 1 are made by injection-moulding of transparent plastics. In the example, each part of rotor 1 on either side of a central plane M is separately injection-moulded and the same applies to the top surface 5. The material used is transparent to UV, and in the present case is non-stabilized methyl polymethacrylate, sold by ICI under the registered trade-mark DIAKON. The various injection-moulded parts are preferably cured before being joined together, using pure solvents such as chloroform or dichloroethane. The parts can also be assembled by ultrasonic welding.

Rotor 1 is used as follows: It is placed on the driving plate of an analytical apparatus (not shown). A certain volume of reagent is introduced into the distribution chamber 3 and the rotor is rotated at a first speed of the order of 400 to 600 rpm for 4 to 8 s. At this speed, the liquid in the distribution chamber 3 is ejected by centrifugal force into the portioning cavities 6 and travels by capillary action through the various transfer passages 9 up to their ends, which open into the vertical walls of the respective analytical cells 2, where a stable meniscus forms and thus prevents the air enclosed in cells 2 from flowing out. Since cells 2 are also hermetically sealed, the thus-imprisoned air prevents liquid entering cells 2, since the centrifugal force communicated to the liquid by the rotor at the aforementioned speed of 400–600 rpm is insufficient to overcome the resistance of the volume of air imprisoned in cells 2. The amount of reagent introduced into the distribution chamber 3 has deliberately been made greater than the total volume of the portioning cavities 6, and the result is that an excess of liquid remains after the cavities have been filled. The excess is then expelled along the inclined plane of the top surface of annular wall 10 into the annular collector 12, the bottom of which is formed with apertures 13 allowing the liquid to flow into the various overflow reservoirs 14. As a result, only the portions corresponding to the volumes of cavities 6 remain at the periphery of chamber 3, and the overflow means ensures that the entire volume of cavities 6 is filled as cavity 6 is sized to assure that the quantity of reagent corresponds to that required, the measured volumes are very accurate.

In a second step, the speed of rotor 1 is rapidly increased to 4,000–5,000 rpm for 2–5 seconds. At this speed, the centrifugal force exerted on the portions of liquid retained in cavities 6 is sufficient for the pressure of the liquid to break the meniscus and thus allow the air to escape from cells 2 by passage 9, so that the liquid can progressively enter the cells, droplets of incoming liquid alternating with outgoing air bubbles until all the liquid has been transferred from cavities 6 to cells 2, the transfer occurring simultaneously for all the cells.

If the sample has already been introduced into the cells, the reactions begin and measurement by any usual technique can be made via windows 15 after reducing the rotor speed to 400–600 rpm in order to measure variations in the absorbance of the samples during their reactions, using a well-known method.

If, on the other hand, the samples are not yet in cells 2, they can be introduced into cavities 6 by a pipette. In this case, the volume of the sample must be less than the volume the portioning cavity can contain at rest, since otherwise the various samples would come into contact and mix with each other.

After the samples have been introduced into the portioning cavities, they are simultaneously centrifuged at 4,000–5,000 rpm and driven into the respective cells, and measurement is begun after reducing the rotor speed to 400–600 rpm.

The design of the described analytical rotor is entirely based on retaining the liquid between the portioning chambers 6 and the cells 2, owing to the capillary effect of passages 9, which maintain a cohesive meniscus which in cooperation with the air in the hermetically-sealed cells, prevents air escaping, with the result that liquid cannot be introduced into the cells except by applying a differential pressure sufficient to break the meniscus. On the other hand, the passage for excess liquid into the overflow reservoirs offers considerably lower resistance. Consequently, when cavities 6 are filled up to their respective inlets, the excess liquid is conveyed to reservoirs 14 along the inclined plane of wall 10, the annular duct 12 and the apertures 13, which are dimensioned so that air can escape and liquid can simultaneously enter. Liquid is transferred from the portioning cavities 6 to the cells 2 after increasing the pressure of the liquid as a result of the centrifugal force produced by raising the rotor speed from 400–600 rpm to 4,000–5,000 rpm. This method of transfer communicates force to each portion of liquid and guarantees the complete distribution of liquid in cells 2, thus ensuring that the measurements made in the cells are accurate. By contrast, this result cannot be ensured by transfer in a flow of fluid under pressure, as proposed in prior art. In addition, centrifuging is the conventional method of transfer in this kind of analysis. Of course, other means, different from those described, could be devised for retaining the liquid in the portioning cavities. However, the enormous advantage of the described retaining means is that they are completely static and are obtained only by suitably dimensioning the various parts of the rotor. The rotor can thus be obtained by injection and sticking or welding, i.e. at a price comparable with known analytical rotors. It can be used on existing centrifugal analytical devices and only requires a low-accuracy pipette for introducing the portion of reagent into the distribution chamber 3.

Figure 4:
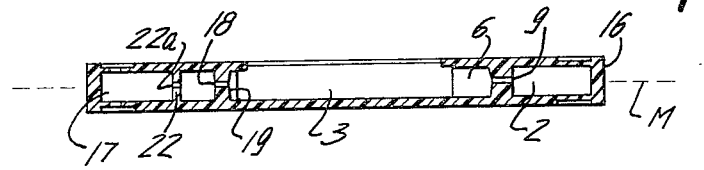
FIG. 4 is a view in section along line IV—IV of FIG. 3.
Figure 3:
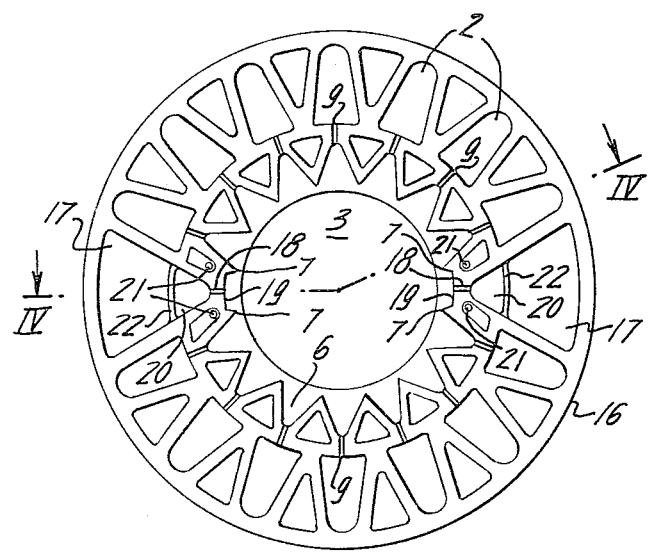
FIG. 3 is a plan view of a second embodiment.

FIGS. 3 and 4 show an embodiment which differs from the preceding mainly in that the analytical rotor 16 has only two, diametrically opposite, overflow reservoirs 17. The portioning cavities 6 and the analytical cells 2 are in every respect similar to those in the preceding embodiment. Consequently, we shall give a detailed description only of the structure of the overflow reservoirs 17, which are connected to the central distribution chamber 3 by respective communicating passages 18 at the ends of recesses 19 each bounded by two of the edges 7 at the intersection between the adjacent sides of the two portioning cavities 6 and the edges of each recess 19, so that the edges of recesses 19 are at the same radial distance from the axis of rotor as the inlets of the various cavities 6.

The interior of the overflow reservoirs 17 is connected to two adjacent lateral chambers 20 near the inlet of the passage 18 into each reservoir 17. Chambers 20 are connected to the external atmosphere by apertures 21 formed through the top surface of rotor 16. As a result, the resistance to liquid entering reservoir 17 is lower than at the inlet of cells 2, since reservoirs 17 communicate with atmosphere via apertures 21 whereas the cells are hermetically sealed as soon as liquid blocks the transfer passages 9.

During low-speed centrifuging (400–600 rpm), the reagent introduced into the chamber 3 is driven into cavities 6 and recesses 19. Since two flows occur through passages 18 and all the edges 7 are along a single radius, the excess liquid inside the radius through edges 7 flows towards recesses 19 and into reservoirs 17.

The air volume corresponding to the volume of the introduced liquid escapes freely to atmosphere via apertures 21. The barriers extend from one edge to the other of the reservoir, leaving an intermediate passage 22a. They are adapted to prevent liquid flow back during the subsequent operations of mixing the liquid reagent and the sample, by oscillation of the analytical rotor.

Figure 5:
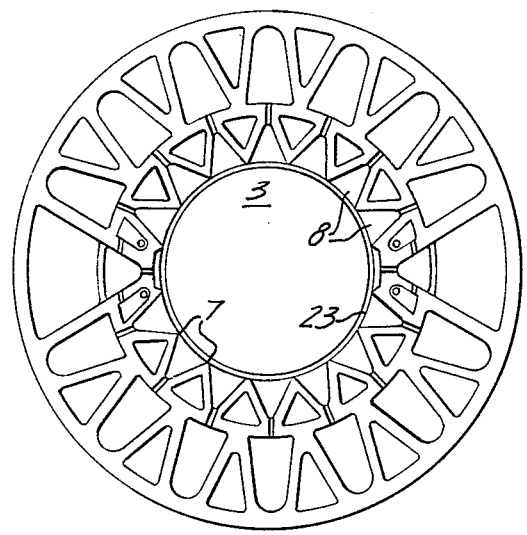
FIGS. 5 and 6 are plan views of two variants of FIG. 3.

FIG. 5 shows a varient, the only difference from the embodiment in FIGS. 3 and 4 being the presence of circular grooves 23 formed in the bottom and top wall of chamber 3 and adjacent edges 7. The grooves are adapted to help the meniscus to stick in the inlet 8 of the proportioning cavities 6, thus improving the portioning accuracy.

Figure 7:
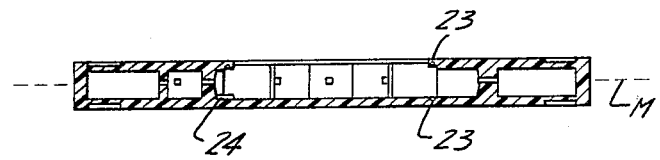
FIG. 7 is a view in section along line VII—VII of FIG. 6.
Figure 6:
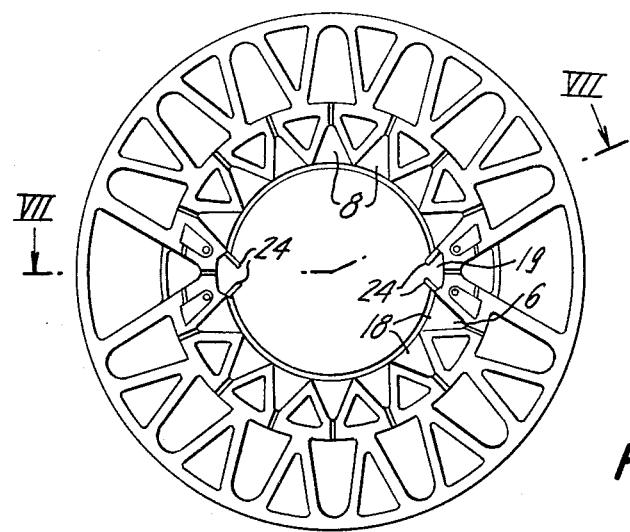

FIGS. 6 and 7 illustrate another variant of FIGS. 3 and 4. In addition to grooves 23, the varient comprises a pair of ribs 24 disposed in line with each side of cavities 6 adjacent the recesses, the ribs being formed at the bottom of chamer 3. Ribs 24 are adapted to slow down the flow of liquid towards recesses 19. The recesses can modify the meniscus at inlets 8 of the adjacent cavities 6 and thus slightly distort the portions, but this is prevented by ribs 24. It must be remembered that the aim of the invention is to attain accuracy of the order of 1% or even below, so that any source of error must be eliminated.

Tests performed with the described rotors show that these make it possible to attain the aforementioned accuracy and reduce the error factor below 1%, thus equalling the accuracy of the best known pipettes. In addition, the method of portioning is not affected by any faults in operation, since the portioning does not result from the action of any moving part and the rotors are used only once and come from a single mould.

The rotors described in connection with FIGS. 3–7 are made by injection-moulding a top and bottom part having substantially equal thickness and stuck or welded by ultra-sound as previously explained.

Figure 8:
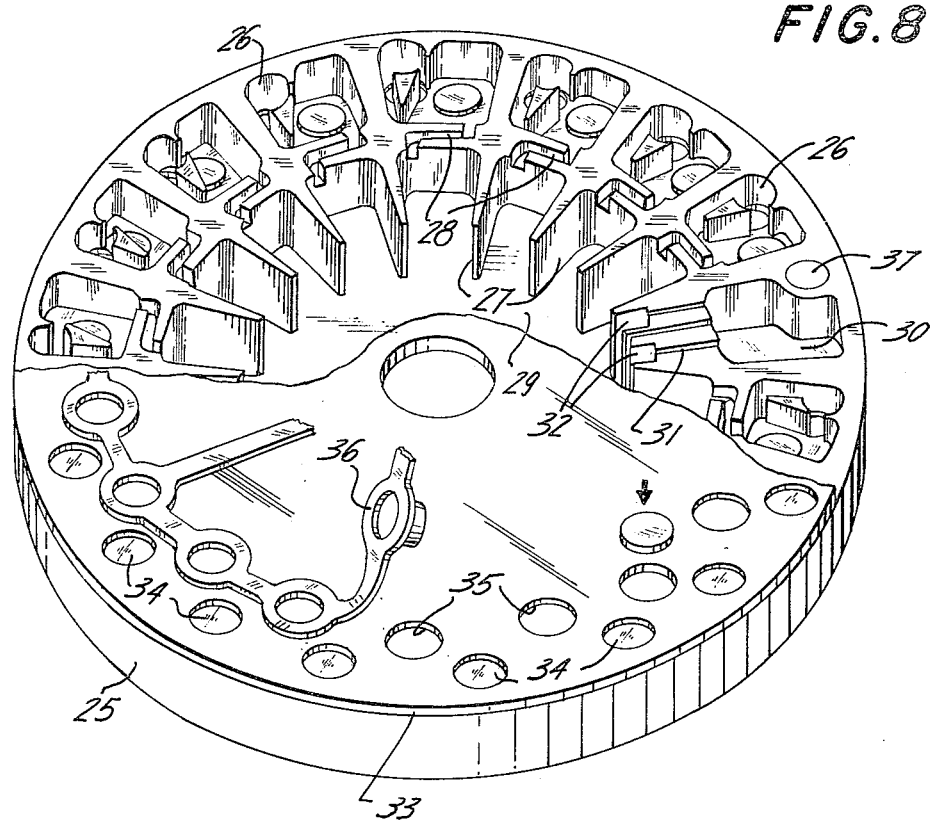
FIG. 8 is a perspective view of a third embodiment.

FIG. 8 shows an embodiment of a rotor 25 especially designed for bacteriological analysis. Rotor 25 has analytical cells 26 connected to a portioning cavity 27 by passages 28. The centre of the rotor is occupied by a distribution chamber 29 towards which all the inlets of the portioning cavities 27 extend. An overflow reservoir 30 occupies the position of an analytical cell 26 and is connected to the distribution chamber 29 by three passages 31, two of which open into chamber 29 via respective recesses 32 at the ends of the passages, so as to collect the surplus liquid and enable it to flow through them, whereas the duct 31 which does not open into a similar recess enables air to escape from reservoir 30 towards the distribution chamber 29 after the excess liquid has entered the reservoir. This feature avoids any contact with the exterior, which is important in the case of bacteriological analysis. On the other hand, the air leaving duct 31 forms foam which may slightly reduce accuracy. In the case, however, of bacteriological analysis, accuracy is less important than the risk of contamination.

The top surface of rotor 25 is covered by a stuck or welded plate 33. As before, the plate has an analysis window 34 coinciding with a similar window formed in the bottom of each cell 26. Plate 33 also has apertures 35, e.g. for introducing an antibiotic product for testing in the presence of a given bacterial strain. A closure means 36 is provided for hermetically closing cells 26 after the product for testing has been inserted. The product is preferably placed on a holder in the form of a hydrophilic paper disc of the kind sold under the registered trade mark "Sensi-disc" by Becton, Dickinson & Co. A culture broth is introduced into the distribution chamber 29 in the same manner as the reagent in the preceding embodiments, and is centrifuged at a first speed in order to fill the portioning cavities 27. The excess liquid is guided by recesses 32 into passages 31, whereas the air comes out by the passage 31 without a recess 32. Once all the excess liquid has been transferred to the overflow chamber 30, the speed of rotor 25 is increased as before in order to drive the portions of liquid into cells 26. Cell 37 (beside chamber 30) is used as reference cell.

Alternatively, the rotors can be sold after filling the cells with given antibiotic products, thus relieving the user of this task. The presence of the transfer passages 28 adjacent plate 33 reduces the stability of the meniscus at the outlets of the aforementioned passages, but simplifies the manufacture of rotor 25, which can be made in one piece by injection-moulding. In this case, an ordinary plate 33 formed with apertures 35 and a window is sufficient to close the top of the assembly of cells 26 and chambers 27. The accuracy obtained with the last-mentioned embodiment is quite compatible with the accuracy required for bacteriological analysis. In the case of a pre-loaded rotor, the apertures 35 can be eliminated, in which case the cells are filled before plate 33 is welded or stuck on.

Figure 9:
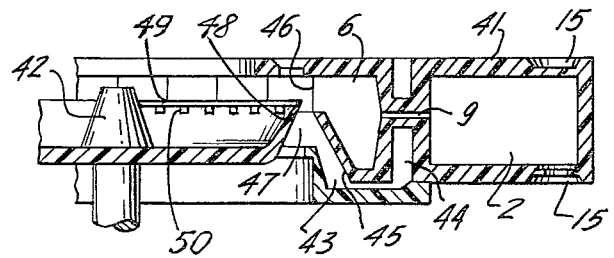
FIGS. 9 and 10 are views in section of a fourth embodiment.
Figure 10:
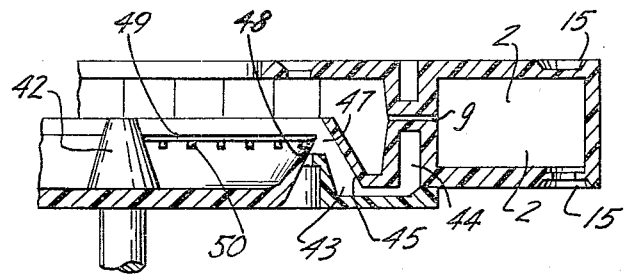

The embodiment shown in FIGS. 9 and 10 essentially differs from the embodiments described above on the one hand in the disposition of the overflow reservoir, and on the other hand in the disposition of the distribution chamber with respect to the other parts of the rotor.

The rotor shown in FIG. 9 consists of a distribution chamber 42 which is apt to receive the liquid to be portioned and distributed by centrifugation and of an assembly 41 comprising portioning cavities 6, transfer passages 9, analytical cells 2, an annular overflow reservoir 44 disposed at the lower part of the assembly and a communication passage 43 leading to the overflow reservoir. This passage comprises an annular collector 43 formed and disposed below the portioning cavities. This collector has an inlet 47 and is separated from the portioning cavities by an annular wall 45, which extends from the lower edge of the inlets 46 of said cavities to the overflow reservoir.

As shown in FIGS. 9 and 10, with respect to the assembly 41, the central distribution chamber 42 can take two positions along the rotational axis of the rotor:

A first position, shown in FIG. 9, in which the radially outermost upper edge 48 of said chamber is at a level comprised between the levels of the upper and the lower edges of the inlets 46 of the portioning cavities 6; and a second position in which said upper edge of the chamber 42 is at a level comprised between the levels of the upper and the lower edges of the inlets 47 of the annular collector 43.

The change from the first position to the second can be obtained by displacing the chamber 42 with respect to the assembly 41 or vice versa.

The rotor shown in FIGS. 9 and 10 is used as follows: It is placed on the driving plate of an analytical apparatus (not shown). A volume of liquid greater than the total volume of the portioning cavities 6 is introduced into the central distribution chamber 42. With this chamber in its first portion (shown in FIG. 9), the rotor is rotated at a first speed of about 600 rpm for 4 to 8 s. At this speed, the liquid in the distribution chamber 42 is ejected by centrifugal force into the portioning cavities 6 and travels by capillary action through the various transfer passages 9 up to their ends, which open into the vertical walls of the respective analytical cells 2, where a stable meniscus forms and thus prevents the air enclosed in cells 2 from flowing out. Since cells 2 are also hermetically sealed, the thus-imprisoned air prevents liquid entering cells 2, since the centrifugal force communicated to the liquid by the rotor at the aforementioned speed of about 600 rpm is insufficient to overcome the resistance of the volume of air imprisoned in cells 2. As the amount of reagent introduced into the distribution chamber 3 has deliberately been made greater than the total volume of the portioning cavities 6, an excess of liquid remains after these cavities have been filled. The excess is then expelled into the annular collector 43 which allows the liquid to flow into the overflow reservoir 44. Consequently, only the portions corresponding to the volumes of cavities 6 remain in that cavities. In this way, the overflow means ensures that the entire volume of cavities 6 is filled, with the result that the measured volumes are very accurate. In a further step, the chamber 42 is put in the second position (shown in FIG. 10) and the speed of the rotor is rapidly increased to 4,000-5,000 rpm for 2-5 seconds. At this speed, the centrifugal force exerted on the portions of liquid retained in cavities 6 is sufficient for the pressure of the liquid to break the meniscus and thus allow the air to escape from cells 2 by passage 9, so that the liquid can progressively enter the cells, droplets of incoming liquid alternating with outgoing air bubbles until all the liquid has been transferred from cavities 6 to cells 2, the transfer occurring simultaneously for all the cells.

If the sample has already been introduced into the cells, the reactions begin and measurement can be made via windows 15 after reducing the rotor speed to about 600 rpm in order to measure variations in the absorbance of the samples during their reactions, using a well-known method.

The embodiment described above with reference to FIGS. 9 and 10 is particularly advantageous when due to the properties of the liquid treated, it can be expected that some drops of liquid remain adhered to the central receptacle of the distribution chamber at the end of the initial centrifugation of the rotor at about 600 rpm. While such drops would be erratically expelled into the analytic cells during the transfer step (centrifugation at about 4,000-5,000 rpm) in the embodiments described above with reference to FIGS. 1-8, this cannot happen in the embodiments described with reference to FIGS. 9-10, since in this embodiments such excess drops are certainly expelled into the overflow reservoir during the transfer step. A similar effect can also be obtained without having to provide the secod position (shown in FIG. 10) of chamber 42, i.e. leaving it in the first position during the transfer step, provided that during the initial centrifugation step at about 600 rpm the chamber 42 is rotated at a greater speed than the assembly 41. In this alternative embodiment the chamber 42 rotates e.g. at about 1,000-1,500 rpm during the initial centrifugation step, while the assembly 41 is rotated at about 600 rpm. During the transfer step, the chamber 42 remains in the position shown in FIG. 9 and is preferably at rest, while the assembly 41 is rotated at about 4,000 rpm in order to transfer the liquid portions from the portioning cavities to the respective analytic cells.

In a preferred embodiment of the rotor shown in FIGS. 9 and 10, the rotor chamber 42 has an annular cover 49, e.g. a disc with a circular opening in the middle and attached to the assembly 41, and lateral apertures 50 with a diameter of about 0,5 mm uniformly disposed along the periphery of the chamber. These features assure an even more uniform distribution of liquid to the portioning cavities 6. A thin slit between cover 49 and chamber 42 can replace the apertures 50.

The aforementioned invention can be used for simultaneously supplying a number of portions, with an accuracy within 1%. Consequently, the portioning means not only replaces the most accurate pipettes but saves considerably time compared with the use of a pipette to load the rotor. The invention, therefore, saves investment by replacing the precision pipette and increases productivity as a result of the simultaneous portioning. These advantages have hitherto been associated with various disadvantages which particularly affected accuracy, inter alia in the case of clinical chemical analyses. The main advantage of the invention is to solve the problem of portioning without using a pipette but with rigorous accuracy comparable with that of the most accurate pipettes, by using static means resulting from the design of the rotor which, like known rotors, can be made in two or three injection-moulded pieces, which are assembled by sticking or welding. Consequently the analytical rotors can be mass-produced at a price which is completely competitive with other analytical rotors which do not incorporate portioning means.

We claim:

1. An analytical centrifugal rotor adapted to receive a liquid comprising
    (a) rotor means;
    (b) a concentric array of analytical cells disposed at the periphery of the rotor, each cell having only one aperture which is normally open and is the inlet of the cell;
    (c) a single central distribution chamber means in said rotor means and having a single inlet for receiving the liquid to be distributed to all analytical cells of said array;
    (d) a concentric array of portioning cavities, each portioning cavity being adjacent to the central distribution chamber means and being disposed between the outer periphery of that distribution chamber means and one of the analytical cells, each portioning cavity having an inlet which is the centripetal open end thereof which directly communicates with the central distribution chamber means over the entire cross-section of said open end without any intervening passageway and an outlet, said open end of each cvity having a cross-section greater than said outlet, the projections of the inlets of all the portioning cavities on a plane perpendicular to the rotation axis of the rotor lying on a circumference the center of which is on the rotation axis of the rotor means;

(e) a plurality of ducts, each duct communicating the outlet of the portioning cavity with the inlet of one of the analytical cells, each duct being formed in a wall which separates the portioning cavity from the corresponding analytical cell, and each duct being configured and dimensioned so as to produce capillary forces in the liquid in order to produce a cohesive meniscus at the centrifugal end of the duct; and (f) at least one overflow reservoir in communication with the central distribution chamber means by passageway means that is not connected to the ducts communicating the analytical cell and the portioning cavities, the projection of the centripetal end of the passageway means on said plane which is perpendicular to the rotation axis of the rotor means falling also on said circumference.

2. A rotor as defined in claim 1, characterized in that the portioning cavities alternate with overflow reservoirs, and in that the passageway means communicating the central distribution chamber means with the overflow reservoirs comprises an annular collector disposed adjacent to the overflow reservoirs, and having in its bottom apertures communicating with the respective reservoirs, and an annular wall covering the portioning cavities and extending from the upper edge of their inlet to the annular collector.

3. A rotor as defined in claim 2, characterized in that the top surface of the annular wall covering the portioning cavities forms an edge with the upper edge of the inlet apertures of the portioning cavities.

4. A rotor as defined in claim 1, characterized in that each duct opens into a surface of the respective cell, the surface being substantially parallel to the axis of rotation of the rotor means and at a distance from the top and bottom surfaces of the cell.

5. A rotor as defined in claim 1, characterized in that it comprises two diametrically opposite overflow reservoirs.

6. A rotor according to claim 1, characterized in that the portion of the cavity into which the duct opens forms an angle smaller than 180° and substantially symmetrical around a radius extending through the centripetal end of the duct.

7. A rotor as defined in claim 1, characterized in that the analytical cells have a constant height whereas their width decreases in proportion to the radial distance from the center of the rotor means.

8. A rotor as defined in claim 1, characterized in that the inlets of the portioning cavities are at a higher level than the bottom of the distribution chamber means and the bottom of the portioning cavities.

9. A rotor as defined in claim 1, characterized in that each cell has a normally closed aperture which is closed with a closure means which is removable from the aperture.

10. A rotor as defined in claim 1, characterized in that the overflow reservoir is disposed between two of the said cavities and is connected to atmosphere by at least one aperture formed in the top surface of the reservoir.

11. A rotor as defined in claim 1, characterized in that circular grooves are formed in the top and bottom rotor means surfaces adjacent to edges formed between the portioning cavities, the grooves cooperating with the inlets of the portioning cavities for determining the position of a liquid meniscus formed at each of those inlets.

12. A rotor as defined in claim 10 or 11, characterized in that the circular grooves formed in the bottom surface of the rotor means are interrupted by ribs disposed on either side of the passageway means communicating with the overflow reservoir, the ribs extending inside the circle bounded by the grooves.

13. An analytical rotor as defined in claim 1, characterized in that the passageway means communicating the central distribution chamber means with the overflow reservoir comprises an annular collector disposed below the portioning cavities, said collector having an inlet with upper and lower edges, an annular wall separating the portioning cavities from said collector and extending from the lower edge of the inlets of said cavities to the overflow reservoir.

14. An analytical rotor as defined in claim 13, characterized in that with respect to an assembly comprising the analytical cells and the portioning cavities the central distribution chamber means can take two positions along the rotation axis of the rotor means:

a first position in which the radially outermost upper edge of said chamber means is at a level comprised between the levels of the upper and the lower edges of the inlets of the portioning cavities, and a second position in which said upper edge of the chamber means is at a level comprised between the levels of the upper and the lower edges of the inlet of the annular collector.

15. An analytical rotor as defined in claim 13, wherein the central distribution chamber means is an element which can rotate at a speed which differs from the rotation speed of an assembly comprising the analytical cells and the portioning cavities and also remains at rest during centrifugation of said assembly.

* * * * *